US010201481B2

(12) United States Patent
Smith, III et al.

(10) Patent No.: US 10,201,481 B2
(45) Date of Patent: *Feb. 12, 2019

(54) PERSONAL CARE COMPOSITIONS AND METHODS OF MAKING SAME

(71) Applicant: The Proctor & Gamble Company, Cincinnati, OH (US)

(72) Inventors: Edward Dewey Smith, III, Mason, OH (US); Jason Edward Cook, Anderson Township, OH (US); Darren Wei-Bun Tang, Montgomery, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/639,686

(22) Filed: Mar. 5, 2015

(65) Prior Publication Data
US 2015/0250696 A1 Sep. 10, 2015

Related U.S. Application Data

(60) Provisional application No. 61/949,849, filed on Mar. 7, 2014.

(51) Int. Cl.
| | | |
|---|---|---|
| A61K 8/02 | (2006.01) | |
| A61K 8/27 | (2006.01) | |
| A61K 8/04 | (2006.01) | |
| A61K 8/49 | (2006.01) | |
| A61Q 19/00 | (2006.01) | |
| A61Q 19/10 | (2006.01) | |
| A61Q 17/00 | (2006.01) | |

(52) U.S. Cl.
CPC ............ *A61K 8/0241* (2013.01); *A61K 8/044* (2013.01); *A61K 8/27* (2013.01); *A61K 8/4933* (2013.01); *A61Q 19/00* (2013.01); *A61K 2800/30* (2013.01); *A61K 2800/412* (2013.01); *A61Q 17/005* (2013.01); *A61Q 19/10* (2013.01)

(58) Field of Classification Search
None
See application file for complete search history.

(56) References Cited

U.S. PATENT DOCUMENTS

| | | |
|---|---|---|
| 3,235,455 A | 2/1966 | Judge et al. |
| 3,281,366 A | 10/1966 | Judge et al. |
| 3,725,547 A | 4/1973 | Kooistra |
| 4,345,080 A | 8/1982 | Bolich, Jr. |
| 4,379,753 A | 4/1983 | Bolich, Jr. |
| 4,565,693 A | 1/1986 | Marschner |
| 4,708,863 A | 11/1987 | Bews et al. |
| 5,037,818 A | 8/1991 | Sime |
| 5,104,645 A | 4/1992 | Cardin et al. |
| 5,106,609 A | 4/1992 | Bolich, Jr. et al. |
| 5,284,649 A | 2/1994 | Juneja |
| 5,540,860 A | 7/1996 | Hosseini et al. |
| 5,573,699 A | 11/1996 | Jones et al. |
| 5,612,301 A | 3/1997 | Inman |
| 5,834,409 A | 11/1998 | Ramachandran et al. |
| 5,886,031 A | 3/1999 | Shin et al. |
| 6,015,547 A | 1/2000 | Yam |
| 6,017,548 A | 1/2000 | Epstein et al. |
| 6,017,562 A | 1/2000 | Kaufman et al. |
| 6,017,936 A | 1/2000 | Polson et al. |
| 6,096,297 A | 8/2000 | Jones et al. |
| 6,150,312 A | 11/2000 | Puvvada et al. |
| 6,162,446 A * | 12/2000 | Hani ..................... A01N 43/40 424/401 |
| 6,214,363 B1 | 4/2001 | Beerse et al. |
| 6,217,887 B1 | 4/2001 | Beerse et al. |
| 6,242,007 B1 | 6/2001 | Mohseni et al. |
| 6,277,360 B1 | 8/2001 | Carew et al. |
| 6,432,432 B1 | 8/2002 | Mohseni et al. |
| 6,451,300 B1 | 9/2002 | Dunlop et al. |
| 6,465,015 B1 | 10/2002 | Mohseni et al. |
| 6,649,155 B1 | 11/2003 | Dunlop et al. |
| 6,673,756 B2 | 1/2004 | Sonnenberg et al. |
| 6,682,724 B2 | 1/2004 | Mohseni et al. |
| 6,887,859 B2 | 5/2005 | Clapp et al. |
| 6,974,569 B2 | 12/2005 | Dunlop et al. |
| 7,001,594 B1 | 2/2006 | Peffly et al. |
| 7,026,308 B1 | 4/2006 | Gavin et al. |
| 7,381,415 B2 | 6/2008 | Yokoyama et al. |
| 7,544,367 B2 | 6/2009 | Mohseni et al. |
| 7,569,530 B1 | 8/2009 | Pan et al. |
| 7,674,785 B2 | 3/2010 | Gavin et al. |
| 8,105,996 B2 | 1/2012 | Wei et al. |
| 8,119,168 B2 | 2/2012 | Johnson et al. |

(Continued)

FOREIGN PATENT DOCUMENTS

| | | |
|---|---|---|
| DE | 195 37 509 A1 | 4/1997 |
| EP | 0034385 A2 | 8/1981 |

(Continued)

OTHER PUBLICATIONS

International Search Report PCT/US2012/050882 and Written Opinion of the International Searching Authority dated Feb. 7, 2014, 11 pages.

Cutler, "How to avoid dry skin from frequent hand washing," available online May 14, 2008; http://www.integrativehealthcare.org/mt/archives/2008/05/5_solutions_how.html.

Fulmer et al., "Stratum Corneum Lipid Abnormalities in Surfactant-Induced Dry Scaly Skin," Journal of Investigative Dermatology 86(5):598-602, 1986.

International Search Report and Written Opinion of the International Searching Authority PCT/US2015/018793 dated May 7, 2015, 11 pages.

(Continued)

*Primary Examiner* — Monica A Shin

(57) ABSTRACT

Personal care compositions include a zinc-containing material and/or a pyrithione material, and are substantially free of a structurant. Methods of making the personal care composition and for improving skin health are also provided herein.

8 Claims, No Drawings

(56) References Cited

U.S. PATENT DOCUMENTS

| | | | |
|---|---|---|---|
| 8,491,877 B2 | 7/2013 | Schwartz et al. | |
| 2002/0176891 A1* | 11/2002 | Dow | A61K 9/0014 424/487 |
| 2003/0068289 A1 | 4/2003 | Bailey et al. | |
| 2003/0165546 A1* | 9/2003 | Resch | A61K 8/34 424/401 |
| 2004/0057920 A1 | 3/2004 | Focht et al. | |
| 2004/0161435 A1 | 8/2004 | Gupta | |
| 2004/0191331 A1 | 9/2004 | Schwartz et al. | |
| 2004/0213751 A1 | 10/2004 | Schwartz et al. | |
| 2005/0020468 A1 | 1/2005 | Frantz et al. | |
| 2005/0118276 A1 | 6/2005 | Lei et al. | |
| 2005/0244352 A1 | 11/2005 | Lemoine et al. | |
| 2006/0079422 A1 | 4/2006 | Midha et al. | |
| 2006/0111259 A1 | 5/2006 | Chakrabarty et al. | |
| 2006/0204467 A1 | 9/2006 | Littau et al. | |
| 2006/0257348 A1 | 11/2006 | Walters et al. | |
| 2006/0275238 A1 | 12/2006 | Blasko-Begoihn et al. | |
| 2007/0009463 A1 | 1/2007 | Niebauer et al. | |
| 2007/0128147 A1 | 6/2007 | Schwartz et al. | |
| 2007/0190177 A1 | 8/2007 | Kling et al. | |
| 2008/0063618 A1 | 3/2008 | Johnson et al. | |
| 2008/0138442 A1 | 6/2008 | Johnson et al. | |
| 2008/0152731 A1 | 6/2008 | Trigiante | |
| 2008/0160093 A1 | 7/2008 | Schwartz et al. | |
| 2008/0166311 A1* | 7/2008 | Modi | A61K 8/731 424/70.1 |
| 2008/0206355 A1* | 8/2008 | Schwartz | A61K 8/27 424/604 |
| 2008/0249136 A1 | 10/2008 | Annis et al. | |
| 2010/0093584 A1 | 4/2010 | Brand et al. | |
| 2011/0039469 A1 | 2/2011 | Cabell et al. | |
| 2011/0197906 A1 | 8/2011 | Schwartz | |
| 2011/0197907 A1 | 8/2011 | Schwarz | |
| 2011/0200649 A1 | 8/2011 | Schwartz | |
| 2011/0200650 A1 | 8/2011 | Schwartz | |
| 2011/0201588 A1 | 8/2011 | Schwartz | |
| 2012/0039966 A1 | 2/2012 | Capretta et al. | |
| 2012/0103151 A1 | 5/2012 | Jones et al. | |
| 2012/0216408 A1 | 8/2012 | Cook et al. | |
| 2012/0219610 A1 | 8/2012 | Smith, III et al. | |
| 2012/0220516 A1 | 8/2012 | Smith et al. | |
| 2012/0246851 A1 | 10/2012 | Smith, III et al. | |
| 2012/0324736 A1 | 12/2012 | Eagleton | |
| 2013/0042482 A1 | 2/2013 | Bradford et al. | |
| 2013/0045248 A1 | 2/2013 | Coffindaffer et al. | |
| 2013/0045255 A1 | 2/2013 | Smith et al. | |
| 2013/0045256 A1 | 2/2013 | Schwartz | |
| 2013/0045257 A1 | 2/2013 | Alwattari et al. | |
| 2013/0045263 A1 | 2/2013 | Smith, III et al. | |
| 2013/0045284 A1 | 2/2013 | Stella | |
| 2013/0045285 A1 | 2/2013 | Stella et al. | |
| 2013/0045907 A1 | 2/2013 | Lanzalaco et al. | |
| 2013/0045961 A1* | 2/2013 | Smith, III | C11D 3/48 514/188 |
| 2013/0048005 A1 | 2/2013 | Smith, III et al. | |
| 2013/0205959 A1 | 8/2013 | Jones et al. | |
| 2013/0222057 A1 | 8/2013 | Henshaw | |
| 2013/0280200 A1 | 10/2013 | Schwartz | |
| 2013/0303503 A1 | 11/2013 | Smith, III et al. | |
| 2014/0274852 A1 | 9/2014 | Jiang et al. | |
| 2014/0303135 A1 | 10/2014 | Smith, III et al. | |
| 2015/0250697 A1 | 9/2015 | Smith, III et al. | |

FOREIGN PATENT DOCUMENTS

| | | |
|---|---|---|
| EP | 0093541 A2 | 11/1983 |
| EP | 0158481 A2 | 10/1985 |
| EP | 0196824 A2 | 10/1986 |
| EP | 0217635 A2 | 4/1987 |
| EP | 0285388 A2 | 10/1988 |
| EP | 0468564 A2 | 1/1992 |
| FR | 2 685 638 A1 | 7/1993 |
| JP | 2006-176675 | 12/2004 |
| WO | 94/14408 A1 | 7/1994 |
| WO | 94/14409 A1 | 7/1994 |
| WO | WO 99/51193 A1 | 10/1999 |
| WO | 99/66886 A1 | 12/1999 |
| WO | WO 99/66886 A1 | 12/1999 |
| WO | 02/00178 A1 | 1/2002 |
| WO | 2006/110386 A1 | 10/2006 |
| WO | WO 2015/090857 A1 | 6/2015 |

OTHER PUBLICATIONS

International Search Report and Written Opinion of the International Searching Authority PCT/US2015/018794 dated May 6, 2015, 12 pages.

Morrison, "Petrolatum a useful classic," Cosmetics & Toiletries magazine 111:59-69, 1996; http://www.lotioncrafter.com/pdf/Petrolatum_A_Useful_Classic.pdf.

Vaseline "Understanding and Overview of Dry Skin," published online Oct. 6, 2008.

\* cited by examiner

PERSONAL CARE COMPOSITIONS AND METHODS OF MAKING SAME

TECHNICAL FIELD

The present disclosure generally relates to personal care compositions having low concentrations of a zinc-containing material and/or a pyrithione material; and methods of making personal care compositions and for improving skin health.

BACKGROUND

Human health is impacted by many microbial entities or microbials such as germs, bacteria, fungi, yeasts, molds, viruses, or the like. For example, invasion by microbial entities or microbials including various viruses and bacteria cause a wide variety of sicknesses and ailments. To reduce such an invasion, people frequently wash their skin with personal care compositions. Accordingly, it would be desirable to provide certain personal care compositions and methods for improving skin health by applying a zinc-containing material and/or a pyrithione material to the skin of an individual. Further, it would be desirable to provide such personal care compositions and methods in a cost-effective manner.

SUMMARY

In accordance with one example, a personal care composition includes from about 0.001% to about 0.02%, by weight of the personal care composition, of at least one of a zinc-containing material and a pyrithione material. The personal care composition is substantially free of a structurant.

In accordance with another example, a personal care composition includes from about 0.001% to about 0.02%, by weight of the personal care composition, of at least one of a zinc-containing material and a pyrithione material. The at least one of the zinc-containing material and the pyrithione material is formed of particulates and suspended in the personal care composition. The personal care composition has a Péclet Number of less than 1. The average particle size of the particulates is about 0.5 μm. The personal care composition exhibits a viscosity from about 4,500 cP to about 7,500 cP.

In accordance with yet another example, a personal care composition includes zinc pyrithione. The zinc pyrithione is formed of particulates, and the zinc pyrithione particulates are suspended within the personal care composition. The personal care composition is substantially free of a structurant. The personal care composition has a Péclet Number of less than 1.

In accordance with still another example, a method for improving skin health includes applying a personal care composition to at least a portion of one of hair follicles and skin of an individual. The personal care composition includes from about 0.001% to about 0.02%, by weight of the personal care composition, of at least one of a zinc-containing material and a pyrithione material. The personal care composition is substantially free of a structurant.

In accordance with still another example, a method for improving skin health includes applying a personal care composition to at least a portion of one of hair follicles and skin of an individual. The personal care composition comprises from about 0.001% to about 0.02%, by weight of the personal care composition, of zinc pyrithione. The zinc pyrithione is formed of particulates, and the zinc pyrithione particulates are suspended within the personal care composition. The personal care composition has a Péclet Number of less than 1. The average particle size of the zinc pyrithione particulates is about 0.5 μm. The personal care composition exhibits a viscosity from about 4,500 cP to about 7,500 cP.

In accordance with still another example, a personal care composition includes about 0.02% or less, by weight of the personal care composition, of at least one of a zinc-containing material and a pyrithione material. The personal care composition is substantially free of a structurant. The personal care composition maintains at least 0.001% by weight, of at least one of a zinc-containing material and a pyrithione material after about 3 years while stored at substantially ambient conditions.

In accordance with yet another example, a method of making a personal care composition includes diluting a primary raw material, and subsequent to dilution, mixing the diluted primary raw material with one or more secondary raw materials to form a personal care composition. The primary raw material includes at least one of a zinc-containing material and a pyrithione material. The personal care composition having from about 0.001% to about 0.02%, by weight of the personal care composition, of the at least one of a zinc-containing material and a pyrithione material. The personal care composition is substantially free of a structurant.

In accordance with still yet another example, a method of making a personal care composition includes mixing a primary raw material with one or more secondary raw materials to form a personal care composition. The primary raw material includes an active component. The active component includes from about 0.1% to about 50%, by weight of the primary raw material, of at least one of a zinc-containing material and a pyrithione material. The personal care composition includes from about 0.001% to about 0.02%, by weight of the personal care composition, of the at least one of a zinc-containing material and a pyrithione material. The personal care composition is substantially free of a structurant.

DETAILED DESCRIPTION

I. Definitions

As used herein, the following terms shall have the meaning specified thereafter:

"Dry skin" is usually characterized as rough, scaly, and/or flaky skin surface, especially in low humidity conditions and is often associated with the somatory sensations of tightness, itch, and/or pain.

"Non-diseased skin" refers to skin that is generally free of disease, infection, and/or fungus. As used herein, dry skin is considered to be included in non-diseased skin.

"Personal care composition" refers to compositions intended for topical application to skin or hair. Personal care compositions can be rinse-off formulations, in which the product can be applied topically to the skin or hair and then subsequently rinsed within seconds to minutes from the skin or hair with water. The product could also be wiped off using a substrate. In either case, it is believed at least a portion of the product is left behind (i.e. deposited) on the skin. Personal care compositions can also be used as shaving aids. The personal care compositions can be extrudable or dispensable from a package. The personal care compositions can be, for example, in the form of a liquid, semi-liquid cream, lotion, gel, solid, or a combination thereof. Examples of personal care compositions can include but are not limited to bar soaps, shampoos, conditioning shampoos, body washes, moisturizing body washes, shower gels, skin cleansers, cleansing milks, in-shower body moisturizers, pet shampoos, shaving preparations, and cleansing compositions used in conjunction with a disposable cleansing cloth.

"Rinse-off" means the intended product usage includes application to skin and/or hair followed by rinsing and/or wiping the product from the skin and/or hair within a few seconds to minutes of the application step.

"SLS" refers to sodium lauryl sulfate.

"STnS" refers to sodium trideceth(n) sulfate, wherein n can define the average number of moles of ethoxylate per molecule.

"Structurant" refers to a substance/ingredient that renders a personal care composition to be structured.

"Structured" refers to having a rheology that can confer stability on the personal care composition. Generally, a personal care composition can be considered to be structured if particles that are more dense than the continuous phase and large enough to exhibit insignificant Brownian motion do not settle; or if the particles are less dense than the continuous phase, the particles do not rise, or cream, during the product lifetime. A degree of structure can also be determined by characteristics determined by one or more of the following methods: Young's Modulus Method, Yield Stress Method, Zero Shear Viscosity Method, or by an Ultracentrifugation Method described in U.S. Pat. No. 8,158,566. Another rheological technique to measure structure includes creep rheology. A personal care composition can be considered to be structured if the personal care composition has one or more following characteristics: (a) Zero Shear Viscosity of at least 100 Pascal-seconds (Pa-s), at least about 200 Pa-s, at least about 500 Pa-s, at least about 1,000 Pa-s, at least about 1,500 Pa-s, or at least about 2,000 Pa-s; (b) A Structured Domain Volume Ratio as measured by the Ultracentrifugation Method, of greater than about 40%, at least about 45%, at least about 50%, at least about 55%, at least about 60%, at least about 65%, at least about 70%, at least about 75%, at least about 80%, at least about 85%, or at least about 90%; or (c) A Young's Modulus of greater than about 2 Pascals (Pa), greater than about 10 Pa, greater than about 20 Pa, greater than about 30 Pa, greater than about 40 Pa, greater than about 50 Pa, greater than about 75 Pa, or greater than about 100 Pa.

"Substantially free of" refers to about 2% or less, about 1% or less, or about 0.1% or less of a stated ingredient. "Free of" refers to no detectable amount of the stated ingredient or thing.

"Viscosity" refers to the viscosity of a finished product, where the viscosity is measured by using a cone and a plate rheometer and applying a shear rate of 2 s$^{-1}$ to the product.

II. Personal Care Compositions

It has been suggested in the literature that zinc-containing materials and/or pyrithione materials can provide benefits to skin, thus improving skin health. In certain examples, a zinc-containing material, such as zinc pyrithione, can provide improved antimicrobial efficacy and improve skin hydration. Such described benefits are disclosed in U.S. Patent Publication Nos. 2013/0045263 A1; 2013/0045284 A1; 2013/0045285 A1; and 2013/0045961 A1. Moreover, such benefits can be provided to both diseased and non-diseased skin. However, in order to provide such benefits, personal care compositions can require specific concentrations of a zinc-containing material and/or a pyrithione material and be in the form of particulates, such that the particulates have a specific average particle size. Conventional personal care compositions containing zinc-containing material particulates and/or pyrithione material particulates at these concentrations and particle sizes require a structurant to prevent the zinc-containing material particulates and/or the pyrithione material particulates from aggregate and/or separate leading to unwanted sedimentation.

Typical structurants can include a structured surfactant such as sodium trideceth(n) sulfate, hereinafter STnS, wherein n can define average moles of ethoxylation. n can range, for example, from about 0 to about 3, from about 0.5 to about 2.7, from about 1.1 to about 2.5, from about 1.8 to about 2.2, or n can be about 2. When n can be less than 3, STnS can provide improved stability, improved compatibility of benefit agents within the personal care compositions, and increased mildness of the personal care compositions. Examples of the use of STnS are disclosed in U.S. patent application Ser. No. 13/157,665. Other suitable structurants can include hydrogenated castor oil (e.g., Thixcin®); ethylene glycol distearate, and acrylate copolymers (e.g., Aqua SF-1).

However, including structurants in any significant amounts in personal care compositions results in greater manufacturing costs due to longer and more complex processing involved and greater consumption of raw materials. Accordingly, providing a personal care composition which is substantially free of or free of a structurant would reduce such manufacturing costs and provide numerous additional benefits.

The present inventors have discovered that a zinc-containing material and/or a pyrithione material can be used in personal care compositions at certain concentrations and at certain average particle sizes such that a personal care composition can be substantially free of a structurant. For example, at suitable average particle sizes and in suitable concentrations, zinc-containing material particulates and/or pyrithione material particulates (e.g., zinc pyrithione or sodium pyrithione) can remain suspended in a personal care composition. This behavior can be further explained by the Péclet Number associated with a composition having such particulates. The Péclet Number calculated in association with a composition having certain particulates relates gravitational forces to diffusive forces with respect to those particulates in the composition. The Péclet Number can be defined by the following formula:

$$Pe = \frac{\text{Gravitational Forces}}{\text{Diffusive Forces (Brownian Motion)}} = \frac{v_S D_{ZPT}}{D_{Br}}$$

where $v_s$ is the Stokes settling velocity, $D_{ZPT}$ is the diameter of a zinc pyrithione particle (assuming spherical geometry), and $D_{Br}$ is the diffusion coefficient. If the Péclet Number is greater than 1, gravitational forces can exceed diffusive forces and particulates can begin to settle in the personal care composition, allowing for sedimentation to occur.

Typically, personal care compositions can include a zinc-containing material and/or a pyrithione material at such concentrations and average particle sizes that the personal care composition can be opaque in appearance. For example, by employing relatively low concentrations of a zinc-containing material and/or a pyrithione material, opacity of a personal care composition can be reduced and/or substantially eliminated. The personal care compositions described herein can include an effective amount of a zinc-containing material and/or a pyrithione material, be substantially free of a structurant, and have the unexpected benefit of reducing or eliminating opacity.

A. Zinc-Containing and/or Pyrithione Materials

A personal care composition can include a zinc-containing material and/or a pyrithione material. Similarly, a method of improving skin health (e.g., increasing antimicrobial efficacy) can include applying a zinc-containing material and/or a pyrithione material to the skin of an individual. Examples of such zinc-containing materials can include, for example, zinc salts. Examples of zinc salts useful herein include the following: zinc aluminate, zinc carbonate, zinc oxide, zinc phosphates, zinc selenide, zinc sulfide, zinc silicates, zinc silicofluoride, zinc borate, zinc hydroxide, zinc hydroxy sulfate, and combinations thereof.

As set forth above, a zinc-containing material can comprise a zinc salt of 1-hydroxy-2-pyridinethione (known as "zinc pyrithione"), for example, a mercaptopyridine-N-oxide zinc salt. Zinc pyrithione can be made by reacting 1-hydroxy-2-pyridinethione (i.e., pyrithione acid) or a soluble salt thereof with a zinc salt (e.g. zinc sulfate) to form a zinc pyrithione precipitate as illustrated in U.S. Pat. No. 2,809,971 and the zinc pyrithione can be formed or processed into platelet zinc pyrithione using, for example, sonic energy as illustrated in U.S. Pat. No. 6,682,724.

Zinc pyrithione can take the form of particulates, platelets, or a combination thereof. For example, where the zinc pyrithione is introduced as particulate, such particulates may have an average particle size of about 1 μm or less; in certain examples from about 0.05 μm to about 1 μm; in certain examples from about 0.1 μm to about 0.9 μm; in certain examples from about 0.25 μm to about 0.75 μm; and in certain examples about 0.5 μm.

Other non-limiting zinc-containing materials can include zinc-containing layered materials ("ZLM's"). Examples of zinc-containing layered materials useful herein can include zinc-containing layered structures with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLM's) may have zinc incorporated in the layers and/or be components of the gallery ions. Many ZLM's occur naturally as minerals. Common examples include hydrozincite (zinc carbonate hydroxide), basic zinc carbonate, aurichalcite (zinc copper carbonate hydroxide), rosasite (copper zinc carbonate hydroxide) and many related minerals that are zinc-containing. Natural ZLM's can also occur wherein anionic layer species such as clay-type minerals (e.g., phyllosilicates) contain ion-exchanged zinc gallery ions. All of these natural materials can also be obtained synthetically or formed in situ in a composition or during a production process. Another common class of ZLM's, which are often, but not always, synthetic, is layered doubly hydroxides, which are generally represented by the formula $[M^{2+}_{1-x}M^{3+}_{x}(OH)_2]^{x+} A^{m-}_{x/m}.nH_2O$ and some or all of the divalent ions ($M^{2+}$) would be represented as zinc ions (Crepaldi, E L, Pava, P C, Tronto, J, Valim, J B *J. Colloid Interfac. Sci.* 2002, 248, 429-42).

Yet another class of ZLM's can be prepared and is called hydroxy double salts (Morioka, H., Tagaya, H., Karasu, M, Kadokawa, J, Chiba, K *Inorg. Chem.* 1999, 38, 4211-6). Hydroxy double salts can be represented by the general formula $[M^{2+}_{1-x}M^{2+}_{1-x}(OH)_{3(1-y)}]^{+} A^{n-}_{(1=3y)/n}.nH_2O$ where the two metal ion may be different; if they are the same and represented by zinc, the formula simplifies to $[Zn_{1+x}(OH)_2]^{2x+}2x A^-.nH_2O$. This latter formula represents (where x=0.4) and contains common materials such as zinc hydroxychloride and zinc hydroxynitrate. These are related to hydrozincite as well wherein a divalent anion replaces the monovalent anion. These materials can also be formed in situ in a composition or in or during a production process. These classes of ZLM's represent relatively common examples of the general category and are not intended to be limiting as to the broader scope of materials which fit this definition.

Commercially available sources of basic zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union Corp.: New York, N.Y., USA), Zinc Carbonate (Elementis Pigments: Durham, UK), and Zinc Carbonate AC (Bruggemann Chemical: Newtown Square, Pa., USA).

Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

Suitable examples of such pyrithione materials can include zinc pyrithione, sodium pyrithione, pyrithione acid, dipyrithione, chitosan pyrithione, magnesium disulfide pyrithione, and combinations thereof. Pyrithione materials may also include other pyridinethione salts formed from metals such as zinc, copper, tin, cadmium, magnesium, aluminium, and zirconium.

B. Personal Care Compositions

Zinc-containing materials (e.g., zinc pyrithione) and/or pyrithione materials can be applied to the skin through a personal care composition. Such personal care compositions can include rinse-off personal care compositions. Examples of suitable zinc-containing materials and pyrithione materials are described herein. Personal care compositions can have varying levels of zinc-containing material and/or pyrithione material. In certain examples, a personal care composition can include from about 0.001% to about 0.02%, by weight of the personal care composition, of at least one of a zinc-containing material and a pyrithione material. In certain examples, a personal care composition can include from about 0.005% to about 0.02%, by weight of the personal care composition, of at least one of a zinc-containing material and a pyrithione material. In certain examples, a personal care composition can include from about 0.01% to about 0.0175%, by weight of the personal care composition, of at least one of a zinc-containing material and a pyrithione material. In certain examples, a personal care composition can include about 0.015%, by weight of the personal care composition, of at least one of a zinc-containing material and a pyrithione material.

As described herein, a zinc-containing material and/or a pyrithione material can be included in a personal care composition at certain concentrations and at certain average particle sizes such that the personal care composition can be substantially free of a structurant. In certain examples, the personal care composition can be free of a structurant. In certain examples, the zinc-containing material and/or the pyrithione material can be suspended in the personal care composition. This phenomenon can be further explained by evaluating the Péclet Number associated with a particular personal care composition. For example, zinc pyrithione particulates can be suspended within a personal care composition having a Péclet Number, as described herein, of less than 1; in certain examples, a Péclet Number of about 0.1 or less; and in certain examples, a Péclet Number of about 0.01 or less.

Moreover, the viscosity of the personal care composition can impact the separation and suspension of the zinc-containing materials and/or pyrithione materials. In certain examples, a personal care composition can have a viscosity of about 50,000 cP or less; about 40,000 cP or less; about 30,000 cP or less; about 20,000 cP or less; or about 10,000 cP or less. In certain examples, a personal care composition can have a viscosity from about 500 cP to about 10,000 cP, from about 1,500 cP to about 9,000 cP, from about 3,000 cP to about 8,000 cP, or from about 4,500 cP to about 7,500 cP. In one example, the zinc pyrithione particulates can be homogeneously mixed throughout the personal care composition.

A personal care composition can include at least one surfactant. In certain examples, a personal care composition can include from about 1.0% to about 50%, by weight of the at least one surfactant; in certain examples, from about 5% to about 40%, by weight of the at least one surfactant; and in certain examples, from about 10% to about 35% by weight of the at least one surfactant. One such surfactant that can be included in a personal care composition is sodium lauryl sulfate, hereinafter SLS. Suitable examples of SLS are described in U.S. patent application Ser. No. 12/817,786. Such suitable surfactants can also include sodium laureth(n) sulfate, hereinafter SLEnS, wherein n can define average moles of ethoxylation. n can range from about 1 to about 3. It will be appreciated that the addition of such surfactants should not render the personal care compositions, described herein, structured.

A personal care composition can further include from about 0.1% to 20%, by weight of the personal care composition, of a cosurfactant. Cosurfactants can comprise amphoteric surfactants, zwitterionic surfactants, nonionic surfactants, or mixtures thereof. In certain examples, such cosurfactants should not render the personal care composition structured. The personal care composition can include at least one of an amphoteric surfactant and a zwitterionic surfactant. Suitable amphoteric or zwitterionic surfactants can include those described in U.S. Pat. No. 5,104,646 and U.S. Pat. No. 5,106,609.

Amphoteric surfactants can include those that can be broadly described as derivatives of aliphatic secondary and tertiary amines in which an aliphatic radical can be straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378. Other examples of amphoteric surfactants can include sodium lauroamphoacetate, sodium cocoamphoacetate, disodium lauroamphoacetate disodium cocodiamphoacetate, and mixtures thereof. Amphoacetates and diamphoacetates can also be used.

Zwitterionic surfactants suitable for use can include those that are broadly described as derivatives of aliphatic quaternary ammonium, phosphonium, and sulfonium compounds, in which aliphatic radicals can be straight or branched chains, and wherein an aliphatic substituent can contain from about 8 to about 18 carbon atoms such that one carbon atom can contain an anionic group, e.g., carboxy, sulfonate, sulfate, phosphate, or phosphonate. Other zwitterionic surfactants can include betaines, including cocamidopropyl betaine (CAPB).

Nonionic surfactants suitable for use can include those selected from the group consisting of alkyl ethoxylates, alkyl glucosides, polyglucosides (e.g., alkyl polyglucosides, decyl polyglucosides), polyhydroxy fatty acid amides, alkoxylated fatty acid esters, sucrose esters, amine oxides, or mixtures thereof.

Other suitable surfactants or cosurfactants that can generally be used in a personal care composition are described in McCutcheon's: Detergents and Emulsifiers North American Edition (Allured Publishing Corporation 1947) (1986), McCutcheon's, Functional Materials North American Edition (Allured Publishing Corporation 1973) (1992) and U.S. Pat. No. 3,929,678 (filed Aug. 1, 1974).

Other optional additives can be included in a personal care composition, including for example an emulsifier (e.g., non-ionic emulsifier) and electrolyes (e.g., sodium chloride). Example emulsifiers and electrolytes are described in U.S. patent application Ser. No. 13/157,665.

Other non-limiting optional ingredients that can be used in a personal care composition can comprise an optional benefit component that can be selected from the group consisting of thickening agents; preservatives (e.g., Kathon, citric acid, sodium benzoate); antimicrobials; fragrances (e.g., perfume); humectants (e.g., sorbitol); chelators (e.g. such as those described in U.S. Pat. No. 5,487,884 issued to Bisset, et al.); sequestrants; vitamins (e.g. Retinol); vitamin derivatives (e.g. tocophenyl actetate, niacinamide, panthenol); sunscreens; desquamation actives (e.g. such as those described in U.S. Pat. Nos. 5,681,852 and 5,652,228 issued to Bisset); anti-wrinkle/anti-atrophy actives (e.g. N-acetyl derivatives, thiols, hydroxyl acids, phenol); anti-oxidants (e.g. ascorbic acid derivatives, tocophenol) skin soothing agents/skin healing agents (e.g. panthenoic acid derivatives, aloe vera, allantoin); skin lightening agents (e.g. kojic acid, arbutin, ascorbic acid derivatives) skin tanning agents (e.g. dihydroxyacteone); anti-acne medicaments; essential oils; sensates; pigments; colorants; pearlescent agents; interference pigments (e.g such as those disclosed in U.S. Pat. No. 6,395,691 issued to Liang Sheng Tsaur, U.S. Pat. No. 6,645,511 issued to Aronson, et al., U.S. Pat. No. 6,759,376 issued to Zhang, et al, U.S. Pat. No. 6,780,826 issued to Zhang, et al.) particles (e.g. talc, kolin, mica, smectite clay, cellulose powder, polysiloxane, silicas, carbonates, titanium dioxide, polyethylene beads) hydrophobically modified non-platelet particles (e.g. hydrophobically modified titanium dioxide and other materials described in a commonly owned, patent application published on Aug. 17, 2006 under Publication No. 2006/0182699A, entitled "Personal Care Compositions Containing Hydrophobically Modified Non-platelet particle filed on Feb. 15, 2005 by Taylor, et al.) and mixtures thereof. A personal care composition can comprise from about 0.1% to about 4%, by weight of the personal care composition, of hydrophobically modified titanium dioxide. Other such suitable examples of such skin actives are described in U.S. patent application Ser. No. 13/157,665.

Other optional ingredients can be most typically those materials approved for use in cosmetics and that are described in the CTFA Cosmetic Ingredient Handbook, Second Edition, The Cosmetic, Toiletries, and Fragrance Association, Inc. 1988, 1992.

Such optional ingredients as described herein can be categorized or described by their cosmetic and/or therapeutic benefit or their postulated mode of action or function. However, it can be understood that actives and other materials useful herein can, in some instances, provide more than one cosmetic and/or therapeutic benefit or function or operate via more than one mode of action. Therefore, classifications herein can be made for convenience and cannot be intended to limit an ingredient to particularly stated application or applications listed. A precise nature of these optional materials, and levels of incorporation thereof, will depend on the physical form of the composition and the nature of the cleansing operation for which it is to be used. Optional materials can usually be formulated at about 6% or less, about 5% or less, about 4% or less, about 3% or less, about 2% or less, about 1% or less, about 0.5% or less, about 0.25% or less, about 0.1% or less, about 0.01% or less, or about 0.005% or less of a personal care composition.

III. Methods of Use to Improve Skin Health

Personal care compositions can be applied by a variety of means, including by rubbing, wiping or dabbing with hands or fingers, or by means of an implement and/or delivery enhancement device. Non-limiting examples of implements can include a sponge or sponge-tipped applicator, a mesh shower puff, a swab, a brush, a wipe (e.g., wash cloth), a loofah, and combinations thereof. Non-limiting examples of delivery enhancement devices can include mechanical, electrical, ultrasonic and/or other energy devices. A personal care composition may be sold together with such an implement or device. Alternatively, an implement or device can be sold separately but contain indicium to indicate usage with a personal care composition. Implements and delivery devices can employ replaceable portions (e.g., the skin interaction portions), which can be sold separately or sold together with the personal care composition in a kit.

Also included herein are methods for improving skin health (e.g., increasing antimicrobial efficacy). For example, one method can include applying a personal care composition including at least one of a zinc-containing material and a pyrithione material to at least a portion of the body (e.g., hair follicles and/or skin) of a user, where the personal care composition is substantially free of a structurant. The method can further comprise rinsing the personal care composition from the body of the user.

While some compositional components are listed in the methods section for illustration, the personal care compositions in employing such methods can contain any combination of components as described herein.

Certain personal care compositions may require a minimum amount of a zinc-containing material and/or a pyrithione material. For example, in order for a personal care composition to exhibit certain benefits associated with a zinc-containing material and/or a pyrithione material, such a personal care composition may need to maintain at least 10 ppm (0.001 wt %) of the zinc-containing material and/or the pyrithione material during the shelf life a product maintained at certain conditions (e.g., three years at ambient conditions). Zinc pyrithione, for example, can undergo degradation in personal care compositions over time. It will be appreciated by those skilled in the art that conventional methodologies are well-known to determine and predict the level of degradation of zinc-containing materials and/or pyrithione materials over time.

IV. Methods of Making a Personal Care Composition

A personal care composition can be formed by the addition of one or more raw materials. In certain embodiments, a primary raw material can be diluted prior to being added to one or more secondary raw materials to form a personal care composition. The primary raw material can include at least one of a zinc-containing material and a pyrithione material as described herein. In certain examples, the dilution can occur in a 1:1 ratio, in certain examples in a 2:1 ratio, and in certain examples in a 4:1 ratio. In certain examples, the primary raw material can be diluted with water (e.g., deionized water). The primary raw material can be in the form of a slurry or other suitable form. Once dilution occurs, the diluted primary raw material can be mixed with one or more secondary raw materials to form a personal care composition. In certain examples, the personal care composition can have from about 0.001% to about 0.02%, by weight of the personal care composition, of at least one of a zinc-containing material and a pyrithione material, and can be substantially free of a structurant.

In another example, a primary raw material can be formed to have a certain concentration of an active component (e.g., zinc pyrithione particles). For example, a primary raw material can include from about 0.1% to about 50%, by weight of the primary raw material, of at least one of a zinc-containing material and a pyrithione material. In certain examples, from about 1% to about 40%, by weight of the primary raw material, of at least one of a zinc-containing material and a pyrithione material; in certain examples, from about 10% to about 30%, by weight of the primary raw material, of at least one of a zinc-containing material and a pyrithione material; and in certain examples about 25%, by weight of the primary raw material, of at least one of a zinc-containing material and a pyrithione material. The primary raw material can be mixed with one or more secondary raw materials to form a personal care composition. The personal care composition can include from about 0.001% to about 0.02%, by weight of the personal care composition, of the at least one of a zinc-containing material and a pyrithione material, and can be substantially free of a structurant.

V. Procedures

A. Iodine-Based Titration Method

The content of a zinc-containing material and/or a pyrithione material in personal care compositions can be measured by an iodine-based titration method. For example, a mercapto group in zinc pyrithione (ZPT) can be titrated by iodine, which can oxidize it to a disulfide-2,2' dithiobispyridine-1-oxide. If zinc pyrithione has already been oxidized or undergone transformation otherwise so that it no longer possesses the mercapto group, it will not be detectable by the iodine-based titration method described hereinafter.

First, a standardized 0.04 N iodine solution is prepared. Specifically, anhydrous sodium thiosulphate (with a minimum purity of 99%) is oven-dried for 2 hours at 105° C. and then stored in a dessicator. Then, 0.05 g (+/−0.0001 g) of the anhydrous sodium thiosulfate is weighed and placed into the 100 mL polypropylene beaker of an autotitrator, and 50 mL of deionized water is added to form a standard solution. The autotitrator used herein is preferably a Mettler DL25 or Mettler DM140-SC titrator with a platinum ring electrode, which is commercially available from Mettler Toledo Internantional, Inc. (Switzerland), or an equivalent thereof. The autotitrator is set up to titrate the standard sodium thiosulfate solution with the iodine solution that is being standardized. Bubbles are eliminated from the burette of the autotitrator, and titration is commenced. Such procedure is repeated twice more, and the results are averaged to obtain a standardized 0.04 N iodine solution. The % relative standard deviation (RSD) should be less than 1% of the average.

Next, standardized 0.01 N and 0.006 N iodine solutions are prepared. Specifically, standardized 0.01N iodine solution is prepared using 0.10 g (+/−0.0001 g) sodium thiosulphate dissolved in 100 mL deionized water, using 10.0 mL pipetted into the 100 mL autotitrator breaker with 50 mL additional deionized water followed by the titration procedure. Standardized 0.006 N iodine solution is prepared using 3.0 mL of a 0.01 M sodium thiosulphate solution and 40 mL of a solvent (containing 13% v/v hydrochloric acid in 6% v/v butanol), followed by addition of 40 mL of 1:1 hexane/isopropanol. The autotitration procedure is subsequently carried out. The iodine solutions are standardized daily.

4.00 g of the personal care composition is weighed and put into a clean, dry beaker of an autotitrator. 75 mL of hot 6% v/v butanol (which was heated in a boiling-water bath) and 5 mL of concentrated HCl (provided at room temperature) are then added into the beaker. The mixture is agitated vigorously so as to fully dissolve all soluble components. The beaker is subsequently placed in the autotitrator, and bubbles are completely eliminated from the burette.

The titration is then initiated and analyzed while the mixture is still warm. The mixture is vigorously agitated during the titration procedure. For compositions with less than 0.2% of ZPT by weight of the personal care composition, titration is carried out using the 0.006N iodine solution. For compositions with higher ZPT concentrations, the initial starting sample weight can be reduced. Titration can be done either manually or by using autotitration procedure by those with skill in the art.

The ZPT content in the personal care composition is calculated as follows:

$$ZPT\ Content\ (\%) = \frac{Volume\ of\ Iodine\ Solution\ (mL) \times N \times 15.88\%}{Sample\ Weight\ (g)}$$

wherein N is the normality of the standardized iodine solution, and wherein 15.88% is a constant that is derived from:

$$15.88\% = \frac{Molecular\ Weight\ of\ ZPT \times 100\%}{No.\ of\ Pyrithione\ per\ Molecule \times 1000\ mL/L} = \frac{371.6 \times 100\%}{2 \times 1000\ mL/L}$$

The above-described procedure is repeated three times for each personal care composition whose ZPT content is to be measured, and the results are averaged to obtain a final ZPT content in percentage (%) for the specific personal care composition.

All chemical reagents employed hereinabove are high-purity reagents obtained from VWR Scientific (Batavia, Ill., USA) or other scientific chemical suppliers.

B. PéClet Number Calculations

As described herein, the Péclet Number can be defined by the following formula:

$$Pe = \frac{Gravitational\ Forces}{Diffusive\ Forces\ (Brownian\ Motion)} = \frac{v_S D_{ZPT}}{D_{Br}}$$

where $v_s$ is the Stokes settling velocity, $D_{ZPT}$ is the diameter of a zinc pyrithione particle (assuming spherical geometry), and $D_{Br}$ is the diffusion coefficient. The Stokes settling velocity, $v_s$, can be defined by the following formula:

$$v_s = \frac{2}{9}\frac{(\rho_{ZPT} - \rho_f)}{\mu_f} g r_{ZPT}^2$$

where $\rho_{ZPT}$ is the density of zinc pyrithione, $\rho_f$ is the density of the fluid phase, $\mu_f$ is the viscosity of the fluid phase, g is the gravitational constant, and $r_{ZPT}$ is the radius of a zinc pyrithione particle. The diffusion coefficient, $D_{Br}$, can be defined by the following Stokes-Einstein Equation:

$$D_{Br} = \frac{k_B T}{6\pi \mu_f D_{ZPT}}$$

where $k_B$ is the Boltzmann's constant and T is the temperature.

VI. Examples

A. Inventive Example 1 and Comparative Examples 1-4

Table 1 below illustrates formulations for personal care compositions.

TABLE 1

| | % Raw Material | | | | |
| --- | --- | --- | --- | --- | --- |
| | Inventive Example 1 | Comparative Example 1 | Comparative Example 2 | Comparative Example 3 | Comparative Example 4 |
| Ingredient | | | | | |
| Water | Q.S. | Q.S. | Q.S. | Q.S. | 100 |
| Sodium Laureth-3- Sulfate | 23.21 | 23.21 | 23.21 | 23.21 | — |
| Sodium Lauryl Sulfate | 8.62 | 8.62 | 8.62 | 8.62 | — |
| Cocamidopropyl betaine | 3.33 | 3.33 | 3.33 | 3.33 | — |
| Sorbitol | 2.86 | 2.86 | 2.86 | 2.86 | — |
| Citirc acid | 0.15 | 0.15 | 0.15 | 0.15 | — |
| Perfume | 0.60 | 0.60 | 0.60 | 0.60 | — |

TABLE 1-continued

| | % Raw Material | | | | |
|---|---|---|---|---|---|
| | Inventive Example 1 | Comparative Example 1 | Comparative Example 2 | Comparative Example 3 | Comparative Example 4 |
| Sodium benzoate | 0.25 | 0.25 | 0.25 | 0.25 | — |
| Kathon (CMIT:MIT) | 0.05 | 0.05 | 0.05 | 0.05 | — |
| Sodium chloride | 2.00 | 2.00 | 2.00 | 2.00 | — |
| Zinc pyrithione | 0.005, 0.01, 0.015, 0.02 | 0.025, 0.05 | 0.015 | 0.015 | 0.015 |
| Parameter | | | | | |
| Particle Size Distribution (Avg. Particle Size) | 0.5 μm* | 0.5 μm* | 2.5 μm** | <1 μm* | 0.5 μm* |
| $D_{ZPT}$ in Finished Product (Avg. Particle Size) | 0.5 μm | 1.0-2.0 μm | 2.5 μm | 1.0-2.0 μm | 0.5 μm |
| Processing Conditions (by wt.) | 1:1 FPS ZPT Dilution in DI Water | 1:1 FPS ZPT Dilution in DI Water | 1:1 U2 ZPT Dilution in DI Water | No Dilution/ Pre-mixing of ZPT | 1:1 FPS ZPT Dilution in DI Water |
| Formula Viscosity (cP) | 6000 | 6000 | 6000 | 6000 | 1.00 |
| Charge Stabilization | No (10% Active Level Surfactant) | No (10% Active Level Surfactant) | No (10% Active Level Surfactant) | No (10% Active Level Surfactant) | Yes (DI Water) |
| Separation Observed | No | Yes | Yes | Yes | Yes |
| Péclet Number | 0.0601 | 0.9758-15.61 | 38.11 | 0.9758-15.61 | 0.0601 |

*FPS ZPT (Kolon)
**U2 ZPT (Lonza)

Each of the personal care compositions for Inventive Example 1 and Comparative Examples 1-3 was formed by the following process. Note that Inventive Example 1 in Table 1 represents four inventive examples such that one formulation included 50 ppm of zinc pyrithione, one included 100 ppm of zinc pyrithione, one included 150 ppm of zinc pyrithione and the last one included 200 ppm of zinc pyrithione. Because each of these four formulations were identical in composition other than with respect to the zinc pyrithione concentration and they each produced the same results, they were combined and are represented collectively as Inventive Example 1. A similar procedure was used in reporting results for Comparative Example 1, wherein two formulations were actually tested, one at 250 ppm zinc pyrithione and one at 500 ppm zinc pyrithione.

With the exception of Comparative Example 3 (no dilution or premixing of zinc pyrithione), preparation began with the formation of a zinc pyrithione premix, where zinc pyrithione and DI water were added to a beaker while stirring. Then, DI water was added to a mixing vessel. Sodium laureth-3 sulfate, sodium lauryl sulfate, and cocamidopropyl betaine were added to the mixing vessel, followed by agitation of the vessel contents. Perfume was then added and mixed into the mixture for at least 10 minutes. Sodium benzoate was then added and allowed to dissolve into the mixture for at least 2 minutes. Citric acid was used to titrate the mixture until a pH of from about 6.5 to about 7.5 was reached, followed by the addition of Kathon and then the zinc pyrithione premix. The mixture was mixed for at least 5 minutes to allow full dispersion of the zinc pyrithione. Sodium chloride was then added and allowed to dissolve into the mixture for at least 2 minutes. DI water and/or sodium chloride were then added to adjust the viscosity of the mixture, which had a target range of 4,500-7,500 cP. For Comparative Example 4, zinc pyrithione was added to DI water.

As discussed above, the Péclet Number can be indicative of whether particulates can remain suspended in a composition. For some personal care compositions having a Péclet Number of less than 1, particulates may be able to remain suspended in the personal care composition without assistance from a structurant. However, if the Péclet Number is greater than 1, gravitational forces can exceed diffusive forces, particulates may begin to settle in the personal care composition, and separation may be observed. Zinc pyrithione concentration and average particle sizes of the zinc pyrithione proved to be determinative. For example, the Péclet Number for Comparative Example 2, which included zinc pyrithione with an average particle size in finished product of 2.5 μm, was calculated to be 38.11 and separation was observed. Similarly, separation was observed for Comparative Examples 1 and 3, each of which included zinc pyrithione with an average particle size in finished product of 1.0-2.0 μm. A Péclet Number range for each of Comparative Examples 1 and 3 was largely >1. While Comparative Example 3 included a lower concentration of zinc pyrithione (0.015%) than Comparative Example 1 (0.025%, 0.05%), a lack of dilution and premixing allowed for an increased level of aggregation, and thus similar average particle sizes in the finished product. The processing conditions in forming the formulations also appear to have proved determinative. For example, the Péclet Number range for Comparative Example 3, which was formed without dilution or premixing of zinc pyrithione, was largely >1. Thus, separation was observed in Comparative Example 3.

Viscosity of the fluid phase also played a role in determining whether separation occurred. For example, the Péclet Number for each of Inventive Example 1 and Comparative Example 4 was calculated to 0.0601, which is substantially less than 1. While separation was not observed for Inventive Example 1, which exhibited a viscosity of 6,000 cP, separation was observed in Comparative Example 4, which had a viscosity of only 1 cP. Thus, viscosity of the fluid phase can have an effect on the stability of a personal care composition.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The products and methods/processes of the present disclosure can comprise, consist of, and consist essentially of the essential elements and limitations of the invention described herein, as well as any of the additional or optional ingredients, components, steps, or limitations described herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid personal cleansing composition, comprising: from about 0.001% to 0.02%, by weight of the personal care composition, of particulate zinc pyrithione having an average particle size of about 0.5 µm; and from about 5% to about 40%, by weight of the composition, of surfactant, wherein the composition has a Péclet Number of less than 1, and has a viscosity of about 4,500 cP to about 7,500 cP and wherein said particulate zinc pyrithione is suspended in said liquid composition.

2. The liquid personal cleansing composition of claim 1, wherein the surfactant comprises sodium laureth-3 sulfate, sodium lauryl sulfate, or a combination thereof.

3. The liquid personal cleansing composition of claim 2, wherein the surfactant further comprises cocamidopropyl betaine.

4. The liquid personal cleansing composition of claim 3, wherein the composition has Péclet Number of about 0.1 or less.

5. The liquid personal cleansing composition of claim 1, wherein the zinc pyrithione particulates are homogeneously mixed throughout the personal care composition.

6. The liquid personal cleansing composition of claim 1 having a Péclet Number of about 0.01 or less.

7. The liquid personal cleansing composition of claim 1 comprising from about 0.01% to about 0.0175%, by weight of the liquid personal cleansing composition, of the zinc pyrithione.

8. The liquid personal cleansing composition of claim 7 comprising about 0.015%, by weight of the liquid personal cleansing composition, of the zinc pyrithione.

* * * * *